J. E. LEE.

METHOD OF PUTTING UP BANDAGES.

APPLICATION FILED JAN. 4, 1909

Reissued Feb. 16, 1909. 12,920.

WITNESSES

L. H. Grote

M. E. Kerr

INVENTOR

John Ellwood Lee

BY

Hosmer and Adams

ATTORNEYS

THE NORRIS PETERS CO., WASHINGTON, D. C.

UNITED STATES PATENT OFFICE.

JOHN ELLWOOD LEE, OF CONSHOHOCKEN, PENNSYLVANIA, ASSIGNOR TO JOHNSON AND JOHNSON, OF NEW BRUNSWICK, NEW JERSEY, A CORPORATION OF NEW JERSEY.

METHOD OF PUTTING UP BANDAGES.

No. 12,920. Specification of Reissued Letters Patent. Reissued Feb. 16, 1909.

Original No. 905,083, dated November 24, 1908, Serial No. 435,944. Application for reissue filed January 4, 1909. Serial No. 470,887.

*To all whom it may concern:*

Be it known that I, JOHN ELLWOOD LEE, a citizen of the United States of America, residing in Conshohocken, in the county of Montgomery, in the State of Pennsylvania, have invented certain new and useful Improvements in Methods of Putting Up Bandages, of which the following is a specification.

My invention consists of an improved method of putting up surgical bandage material in rolls, so that the bandages shall be thoroughly aseptic, and be well protected until opened for use, but that the package can be readily opened when the contents are needed.

Figure 1:
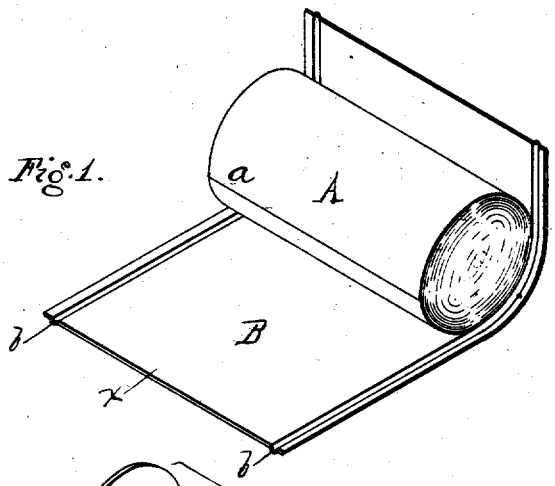
Figure 2:
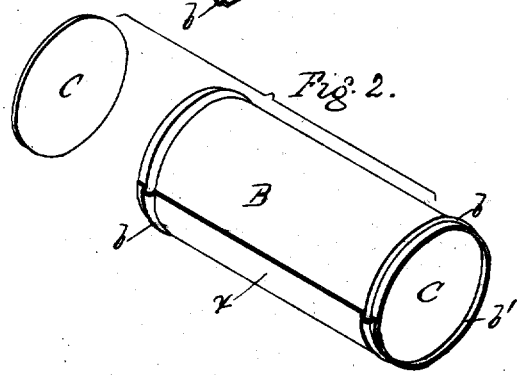
Figure 3:
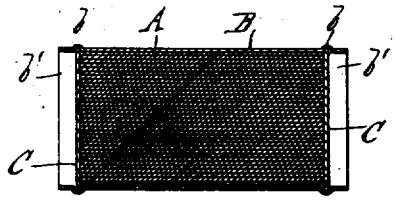
Figure 4:
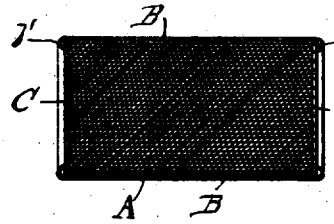

In the accompanying drawings: Figure 1 is a perspective view showing a preliminary stage in the wrapping of the bandage roll; Fig. 2 is a perspective view showing a further stage; Fig. 3 is a longitudinal section of a partially finished package; and Fig. 4 is a similar view of a finished wrapped bandage roll.

The bandage material is preferably wrapped up tightly in long rolls within a light paper wrapper, the overlapping edge of which is sealed by gum or paste. This roll is as long as the width of the woven gauze or other web of material, of which the bandage is to be wrapped, but this long roll is then cut into the desired short lengths, producing a cylindrical roll A, Fig. 1, inclosed within a paper wrapper *a* with the contents exposed at the ends. Each roll section is now wrapped within a sheet of thicker paper B, which is of suitable length for the diameter of the roll and of slightly greater width than the length of the roll. The wrapper is previously formed with grooves *b*, *b*, near each edge at a distance apart equal to the length of the roll A. Gum or paste or other adhesive is applied to the edge *x* where it overlaps the other edge of the wrapper B when rolled up, so as to make a tight longitudinal joint in the rolled up wrapper. There are then inserted into the opposite ends of this rolled wrapper B, card board or thick paper disks C, which are plain, that is, flangeless, and find seats in the grooves *b*, *b*, and are thereby retained in place during the next operation. This succeeding operation consists in spinning down the projecting ends *b'* of this wrapped roll B, Fig. 3, to turn them in to form supporting shoulders bearing against the outer faces of the plain disks as shown in Fig. 4 to hold the disks firmly in place. This operation obliterates the grooves *b*, *b*. By the above described simple method I provide what is found to be a practically hermetically sealed package of surgical bandage, which nevertheless can be readily opened when required to be used.

The turned-in ends of the tubes are not locked to the disks, as is done when the disks have flanges, and there being no other shoulders in the outer wrapper than those formed by the turned-in ends, the package can be easily opened by simply pressing on one of the disks with the thumb or other means, and thereby pushing the bandage roll out of the other end of the package.

I claim as my invention:

1. The method herein described of making surgical bandage rolls, consisting in first forming a length of bandage roll, wrapping this in a sheet of greater width than the length of the roll and sealing the longitudinal joint, inserting plain disks within the opposite ends of this wrapper and then spinning down the ends of the wrapper against the outer faces of the disks.

2. The method herein described of making surgical bandage rolls, consisting in first forming a length of bandage roll, wrapping this in a sheet of greater width than the length of the roll, previously forming grooves in the sheet near its edges at a distance apart equal to the length of the roll, sealing the longitudinal joint of the wrapper, inserting disks within the grooves of the wrapper, and then spinning the ends over the disks and obliterating said grooves.

In testimony whereof I have signed my name to this specification, in the presence of two subscribing witnesses.

JOHN ELLWOOD LEE.

Witnesses:

M. E. WRIGHT,

A. A. BARR.